United States Patent
Sprenger et al.

(10) Patent No.: US 7,115,765 B2
(45) Date of Patent: Oct. 3, 2006

(54) METHOD FOR PRODUCING 6-ALKOXY-(6H)-DIBENZ [C,E] [1,2]-OXAPHOSPHORINES

(75) Inventors: Stephan Sprenger, Oststeinbek (DE); Michael Ciesielski, Merseburg (DE); Carsten Kollann, Stutensee (DE); Manfred Döring, Wörth-Büchelberg (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 10/505,201

(22) PCT Filed: Feb. 12, 2003

(86) PCT No.: PCT/EP03/01368

§ 371 (c)(1),
(2), (4) Date: Apr. 15, 2005

(87) PCT Pub. No.: WO03/070736

PCT Pub. Date: Aug. 28, 2003

(65) Prior Publication Data

US 2005/0176983 A1    Aug. 11, 2005

(30) Foreign Application Priority Data

Feb. 20, 2002  (DE)  ................. 102 06 982

(51) Int. Cl.
*C07F 9/02* (2006.01)
(52) U.S. Cl. ....................................... 558/82
(58) Field of Classification Search ............ 558/82
See application file for complete search history.

(56) References Cited

FOREIGN PATENT DOCUMENTS

| EP | 0304782 | 3/1989 |
| EP | 0787738 | 8/1997 |

OTHER PUBLICATIONS

Qureshi et al., Synthesis and Characterization of Novel 6-Substituted 4-phenyl-6H-dibenz [c,e][1,2] oxaphosphorins, Journal of Chemical Research, 1998, 355.*
Qureshi et al., Synthesis and Characterization of Novel 6-Substituted 4-phenyl-6H-dibenz [c,e][1,2] oxaphosphorins, SYNOPSES, 1998, (7), 1601-1615.*
Chernyshev E A et al: "Organophosphorous Heterocyclic Compounds," Journal of General, New York, US, BD. 42, No. 1,Part 1, 1972, pp. 88-90.

* cited by examiner

*Primary Examiner*—Johann Richter
*Assistant Examiner*—Chukwuma Nwaonicha
(74) *Attorney, Agent, or Firm*—Friedrich Kueffner

(57) ABSTRACT

The present invention relates to a process for preparing 6-alkoxy-(6H)-dibenzo[c,e][1,2]oxaphosphorins, wherein 6H-dibenzo[c,e][1,2]oxaphosphorin 6-oxides of the formula I

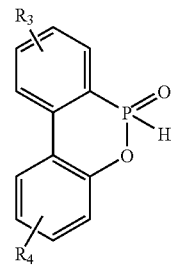

are used as the reactant.

11 Claims, No Drawings

METHOD FOR PRODUCING 6-ALKOXY-(6H)-DIBENZ [C,E] [1,2]-OXAPHOSPHORINES

The present invention relates to the preparation of 6-alkoxy-(6H)-dibenzo[c,e][1,2]oxaphosphorins.

The only method disclosed by the literature for preparing 6-alkoxy-(6H)-dibenzo[c,e] [1,2]oxaphosphorins is the alcoholysis of 6-chloro-(6H)-dibenzo[c,e][1,2]oxaphosphorins in the presence of stoichiometric amounts of base such as tertiary amines or ammonia (EP 0787738 A1, EP 0304782 A2, Phosphorus and Sulfur 1987, 31, p. 71).

Reactions of 6H-dibenzo[c,e] [1,2]oxaphosphorin 6-oxides with orthoformic esters have to date selectively afforded only 6-(dialkoxymethyl)-dibenzo[c,e] [1,2]oxaphosphorin 6-oxides (J. praktische Chemie 1979, 321, p. 361).

The preparation of 6-alkoxy-(6H)-dibenzo[c,e] [1,2]oxaphosphorins by alcoholysis of 6-chloro-(6H)-dibenzo[c,e] [1,2]oxaphosphorins by means of bases entails a two-stage preparation of the 6-chloro derivative from o-hydroxybiphenyl and phosphorus trichloride with an unsatisfactory overall yield of less than 50%. Specifically the second synthetic stage is carried out under metal halide catalysis at temperatures above 200° C. and with HCl elimination. This process places such high requirements on the technology that no industrial solution has to date been attempted. In contrast, 6H-dibenzo[c,e] [1,2]oxaphosphorin 6-oxide is currently even industrially available and is prepared from the same reactants in a one-stage synthesis in yields of above 95% (EP 0806429 A2).

It is thus desirable to develop a process which enables the preparation of 6-alkoxy-(6H)-dibenzo[c,e][1,2]oxaphosphorins by a simple and inexpensive route. They are already known to be useful as additives or modifiers for several polymers and also as intermediates for preparing photoinitiators (EP-B 0292786, 7856250 and EP-A 0304782).

The object of the present invention is achieved by using 6H-dibenzo[c,e] [1,2]oxaphosphorin 6-oxides of the formula I

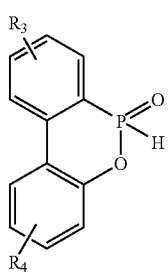

as the reactant.

In general, the process according to the invention includes the following individual steps: 1) providing at least one solvent, 2) adding the reactant, 3) adding an ortho ester, 4) adding alcohol if it is not already present in the form of the solvent.

Useful solvents are methanol, ethanol and nonaromatic substituted alcohols, benzene, alkylated benzenes, aliphatic and cycloaliphatic ethers.

According to the aforesaid, the present invention relates to a process for gently and selectively preparing 6-alkoxy-(6H)-dibenzo[c,e] [1,2]oxaphosphorins by reacting industrially available 6H-dibenzo[c,e][1,2]oxaphosphorin 6-oxides with orthocarboxylic esters, which is acid-catalyzed. The selection of a suitable alcohol as the reaction medium then allows the desired 6-alkoxy-(6H)-dibenzo[c,e][1,2]oxaphosphorin to be obtained by in situ transesterification by means of this alcohol. Accordingly, the reaction may be illustrated as follows:

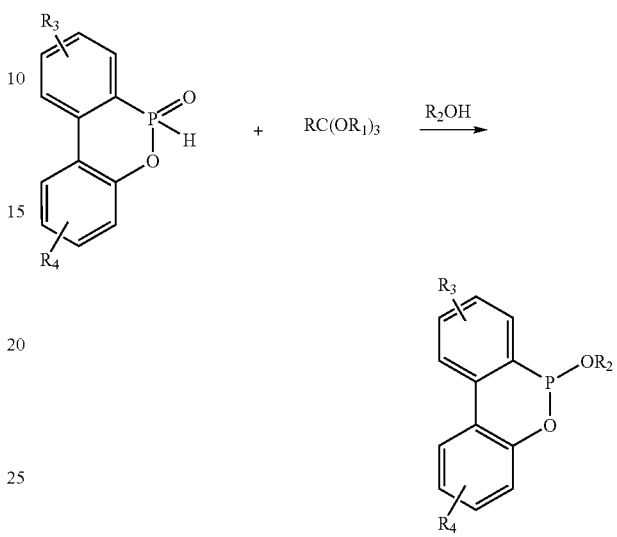

For the $R_1$ and $R_2$ radicals in the above formulae, specific substances which may be used include:

optionally substituted alkyl: saturated, straight-chain or branched hydrocarbon radicals, especially having from 1 to 10 carbon atoms, e.g. C1–C6-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

optionally substituted alkenyl: unsaturated, straight-chain or branched hydrocarbon radicals, especially having from 2 to 10 carbon atoms and a double bond in any position, e.g. C2–C6-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pententyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3,1,1,2-trimethyl-2-propenyl, 1-ethyl-1-methyl-2-propenyl, 1-ethyl-2-methyl-1-propenyl and 1-ethyl-2-methyl-2-propenyl;

optionally substituted alkynyl: straight-chain or branched hydrocarbon groups, especially having from 2 to 20 carbon atoms and a triple bond in any position, e.g. C2–C6-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

an optionally substituted saturated or mono- or diunsaturated ring which, in addition to carbon atoms, may contain from one to three of the following heteroatoms as ring members: oxygen, sulfur and nitrogen, for example carbocycles such as cyclopropyl, cyclopentyl, cyclohexyl, cyclopent-2-enyl, cyclohex-2-enyl, 5- to 6-membered, saturated or unsaturated heterocycles containing from one to three nitrogen atoms and/or one oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

for the $R_3$ and $R_4$ radicals in the above formulae, specific substances which may be used include the following:

alkoxy: straight-chain or branched alkyl groups having from one to 30 carbon atoms (as specified above) which are bonded to the structure via an oxygen atom (—O—).

alkylthio: straight-chain or branched alkyl groups having from one to 30 carbon atoms (as specified above) which are bonded to the structure via a sulfur atom (—S—).

Optionally substituted alkyl as described above for $R_1$ and $R_2$.

Optionally substituted alkenyl as described above for $R_1$ and $R_2$.

Optionally substituted alkynyl as described above for $R_1$ and $R_2$.

An optionally substituted saturated or mono- or diunsaturated ring as described above for $R_1$ and $R_2$.

An optionally substituted mono- or bicyclic aromatic ring system which, in addition to carbon atoms may contain from one to four nitrogen atoms or one or two nitrogen atoms and one oxygen or sulfur atom or one oxygen or sulfur atom as ring members, i.e. aryl radicals such as phenyl and naphthyl, preferably phenyl or 1- or 2-naphthyl, and hetaryl radicals, for example 5-membered heteroaromatic rings containing from one to three nitrogen atoms and/or one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered heteroaromatic rings containing from one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The additional specification "optionally substituted" in relation to alkyl, alkenyl and alkynyl groups is intended to express that these groups may be partially or fully halogenated (i.e. the hydrogen atoms of these groups may be partly or fully replaced by identical or different halogen atoms as specified above (preferably fluorine, chlorine and bromine, in particular fluorine and chlorine), and/or may bear from one to three, in particular one, of the following radicals:

nitro, cyano, C1–C4-alkoxy, C1–C4-alkoxycarbonyl or an optionally substituted mono- or bicyclic aromatic ring system which, in addition to carbon atoms may contain from one to four nitrogen atoms or one or two nitrogen atoms and one oxygen or sulfur atom or one oxygen or sulfur atom as ring members, i.e. aryl radicals such as phenyl and naphthyl, preferably phenyl or 1- or 2-naphthyl, and hetaryl radicals, for example 5-membered heteroaromatic rings containing from one to three nitrogen atoms and/or one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

six-membered heteroaromatic rings containing from one to four nitrogen atoms as heteroatoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

The additional specification "optionally substituted" in relation to the cyclic (saturated, unsaturated or aromatic) groups is intended to express that these groups may be partially or fully halogenated (i.e. the hydrogen atoms of these groups may be partly or fully replaced by identical or different halogen atoms such as mentioned before (preferably fluorine and chlorine), and/or may bear from one to three of the following radicals: nitro, cyano, C1–C4-alkyl, C1–C4-alkoxy and C1–C4-alkoxycarbonyl.

The mono- or bicyclic, aromatic or heteroaromatic systems specified for the radicals may for their part be partially or fully halogenated, i.e. the hydrogen atoms of these groups may be partially or fully replaced by halogen atoms such as fluorine, chlorine, bromine and iodine, preferably fluorine and chlorine.

These mono- or bicyclic, aromatic or heteroaromatic systems may, apart from the halogen atoms referred to, additionally bear from one to three of the following substituents:

nitro, cyano, thiocyanato;
alkyl, particularly C1–C6-alkyl as specified above,
C1–C30-alkoxy,
C1–C30-alkylthio,
C1–C4-alkylamino,
C1–C6-alkylcarbonyl;
C1–C6-alkoxycarbonyl,
C1–C6-alkylaminocarbonyl,
C1–C6-alkylcarboxyl,
C1–C6-alkylcarbonylamino,
C3–C7-cycloalkyl such as cyclopropyl, cyclobutyl, cyclopentyl, cyclohexyl and cycloheptyl, preferably cyclopropyl, cyclopentyl and cyclohexyl, in particular cyclopropyl;
C3–C7-cycloalkoxy such as cyclopropyloxy, cyclobutyloxy, cyclopentyloxy, cyclohexyloxy and cycloheptyloxy, preferably cyclopentyloxy and cyclohexyloxy, in particular cyclohexyloxy;
C3–C7-cycloalkylthio such as cyclopropylthio, cyclobutylthio, cyclopentylthio, cyclohexylthio and cycloheptylthio, preferably cyclohexylthio;
$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino;
further radicals for optionally substituted mono- or bicyclic, aromatic or heteroaromatic radicals:
alkenyl, alkynyl, haloalkenyl, haloalkynyl, alkenyloxy, alkynyloxy, haloalkenyloxy, haloalkynyloxy, alkenyl-thio, alkynylthio, alkylsulfoxy, alkylsulfonyl, alkenylsulfoxy, alkynylsulfoxy, alkynylsulfonyl,
for the present invention, the solvents used are preferably alcohols or alcohol-containing mixtures. The alcohol selected is in particular one in which $R_1$ is different from $R_2$. Useful solvents also include benzene, alkylated benzenes, aliphatic and cycloaliphatic ethers.

One advantage in the selection of an alcohol in which $R_1$ is different from $R_2$ is that it is possible to determine the target molecule $R_2$ radical by the alcohol $R_2$ radical and to use the inexpensive ortho esters.

According to the invention, the reaction is preferably carried out in the presence of a compound capable of ester formation with the reactant. Useful for this purpose are, for example, ortho esters, in particular trialkyl or triaryl ortho esters or lactone acetals.

Preference is accordingly given in accordance with the invention to trialkyl orthoformates. Very particular preference is given to methyl or ethyl orthoformates.

In the individual steps, catalysts may be added. Useful for this purpose are, for example, Lewis acids and Brønsted acids. Particular mention should be made here of proton donors. Examples are hydrogen halides, phosphoric acids, sulfuric acids, and the like. Preference is given to hydrogen halides, in particular hydrochloric acid. The catalysts are preferably recycled.

The resulting products are 6-alkoxy- (or 6-aryloxy)-(6H)-dibenzo[c,e][1,2]oxaphosphorins. The alkoxy groups are preferably methoxy, ethoxy or propoxy radicals.

The process according to the invention enables the preparation of 6-alkoxy-(6H)-dibenzo[c,e][1,2]oxa-phosphorins, especially when the solvent used is alcohol, directly from industrially available 6H-dibenzo[c,e][1,2]oxaphosphorin 6-oxides in one synthetic step with excellent yields. It is advantageous that the fine distillation can be dispensed with under industrial conditions, and a purity of over 96% by GC can be attained in this case.

It is also advantageous that the process according to the invention enables halogen-free working. When, for example, hydrochloric acid is used, it is used merely as a catalyst. In the course of the removal of the excess alcohol, it is also recycled. The consequence thereof is that no halide wastes arise. A further advantage of the present invention is that the reactants used are available inexpensively. Moreover, when the catalysts used are acidic resins, the present invention enables continuous working. Starting from o-hydroxybiphenyl and phosphorus trichloride, it is a two-stage process, whereas three-stage processes are used in the prior art.

The invention is illustrated in detail hereinbelow with reference to the examples:

6-Methoxy-(6H)-dibenzo[c,e][1,2]oxaphosphorin
from 6H-dibenzo[c,e][1,2]oxaphosphorin 6-oxide
and trimethyl orthoformate in methanol 1.33 mol (287.5 g) of 6H-dibenzo[c,e] [1,2]oxaphosphorin 6-oxide and 2.5 ml of conc. HCl are dissolved in 1230 ml of methanol and the mixture is heated to reflux at 85° C. (slightly elevated pressure). After 45 min, a further 0.5 ml of conc. HCl is added, and 2.7 mol (295 ml) of trimethyl orthoformate are subsequently added dropwise within 5 h. During the dropwise addition of the trimethyl orthoformate, in each case 0.5 ml of conc. HCl is added every 30 min. On completion of the reaction, all volatile constituents are removed under reduced pressure on a rotary evaporator. The yellow, oily residue is distilled in fine vacuum (0.1 mbar). At 130–135° C., the product distills as a colorless, oily liquid which solidifies slowly after several weeks. Yield: 265 g, 87% of theory.

6-Ethoxy-6H-dibenzo[c,e][1,2]oxaphosphorin from 6H-dibenzo[c,e][1,2]oxaphosphorin 6-oxide, ethanol and triethyl orthoformate 0.2 mol (43.2 g) of 6H-dibenzo[c,e][1,2]oxaphosphorin 6-oxide and 0.5 ml of conc. HCl are dissolved in 352 ml of ethanol and the mixture is heated to reflux at 90° C. (slightly elevated pressure). After 50 min, a further 0.1 ml of conc. HCl is added, and 0.4 mol (59.3 g, 66.5 ml) of triethyl orthoformate is subsequently added dropwise within 4 h. During the dropwise addition of the triethyl orthoformate, in each case 0.1 ml of conc. HCl is added every 30 min. On completion of the reaction, all volatile constituents are removed under reduced pressure on a rotary evaporator. The yellow, oily residue is distilled in fine vacuum (0.1 mbar). At 135–142° C., the product distills as a colorless, oily liquid (solidified melt $F_p$=42° C.). Yield: 44.8 g, 92% of theory.

6-Ethoxy-6H-dibenzo[c,e][1,2]oxaphosphorin from 6H-dibenzo[c,e][1,2]oxaphosphorin 6-oxide reactant, ethanol and trimethyl orthoformate 5.0 mol (1081 g) of 6H-dibenzo[c,e][1,2]oxaphosphorin 6-oxide and 2.0 ml of conc. HCl are dissolved in 4400 ml of ethanol and the mixture is heated to reflux at 95° C. (slightly elevated pressure). After 1 h, a further 1.0 ml of conc. HCl is added, and 6.5 mol (689.8 g, 711.1 ml) of trimethyl orthoformate are subsequently added dropwise within 8 h. During the dropwise addition of the trimethyl orthoformate, in each case 1.0 ml of conc. HCl is added every 30 min. On completion of the reaction, all volatile constituents are removed under reduced pressure on a rotary evaporator. The yellow, oily residue is distilled in fine vacuum (0.1 mbar). At 135–142° C., the product distills as a colorless, oily liquid (solidified melt $F_p$=42° C.). Yield: 1001.0 g, 82% of theory.

6-Isopropoxy-6H-dibenzo[c,e][1,2]oxaphosphorin from 6H-dibenzo[c,e][1,2]oxaphosphorin 6-oxide reactant, isopropanol and triethyl orthoformate 0.28 mol (59.5 g) of 6H-dibenzo[c,e][1,2]oxaphosphorin 6-oxide are dissolved in 600 ml of isopropanol. 0.6 ml of conc. HCl is added and the mixture heated to reflux at 105° C. (slightly elevated pressure). After 1 h, a further 0.15 ml of conc. HCl is added, and 0.55 mol (81.5 g, 92 ml) of triethyl orthoformate is subsequently added dropwise within 3 h. During the dropwise addition of the triethyl orthoformate, in each case 0.15 ml of conc. HCl is added every 15 min. On completion of the reaction, all volatile constituents are removed under reduced pressure on a rotary evaporator. The yellow, oily residue is distilled in fine vacuum (0.1 mbar). At 142–145° C., the product distills as a colorless, oily liquid. Yield: 35.2 g, 78% of theory.

What is claimed is:

1. A process for preparing 6-alkoxy-(6H)-dibenzo [c,e][1,2] oxaphosphorins, wherein 6H-dibenzo [c,e][1,2]oxaphosphorin 6-oxides of the formula I

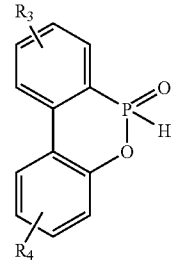

where R3, R4=alkyl, alkoxy, alkylthio, alkenyl, alkynyl, aryl, heteroaryl, cycloalkyl groups are used as the reactant, further comprising, carrying out the following steps:
   1) providing at least one solvent,
   2) adding the reactant
   3) adding an ortho ester and
   4) adding alcohol if it has not already been used under step 1).

2. The process as claimed in claim 1, wherein the solvent used is an alcohol or alcohol-containing mixture.

3. The process as claimed in claim 2, wherein alcohols of the formula $R_2OH$ are used where $R_2$ is alkyl.

4. The process as claimed in claim 1, wherein the reaction is carried out in the presence of a compound capable of ester formation with 6H-dibenzo [c,e][1,2]oxaphosphorin 6-oxides.

5. The process as claimed in claim 1, wherein the reaction is carried out in the presence of a trialkyl orthoformate.

6. The process as claimed in claim 5, wherein the reaction is carried out in the presence of trimethyl or triethyl orthoformate.

7. The process as claimed in claim 1, wherein it is carried out in the presence of catalysts.

8. The process as claimed in claim 7, wherein the catalysts used are Lewis acids or Brønsted acids.

9. The process as claimed in claim 8, wherein the acids used are proton donors.

10. The process as claimed in claim 9, wherein the acids used are hydrogen halides.

11. The process as claimed in claim 1, wherein the excess alcohol is removed and the catalyst is simultaneously recycled.

* * * * *